(12) United States Patent
Fossel

(10) Patent No.: US 9,161,915 B2
(45) Date of Patent: **\*Oct. 20, 2015**

(54) DELIVERY OF IBUPROFEN AND OTHER COMPOUNDS

(71) Applicant: Strategic Science & Technologies, LLC, Cambridge, MA (US)

(72) Inventor: Eric T. Fossel, Cambridge, MA (US)

(73) Assignee: Strategic Science & Technologies, LLC, Cambridge, MA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 14/067,262

(22) Filed: Oct. 30, 2013

(65) Prior Publication Data

US 2014/0056971 A1 Feb. 27, 2014

Related U.S. Application Data

(63) Continuation of application No. 12/812,187, filed as application No. PCT/US2009/003749 on Jun. 24, 2009, now Pat. No. 8,604,081.

(51) Int. Cl.
| | |
|---|---|
| *A61K 31/198* | (2006.01) |
| *A61K 31/715* | (2006.01) |
| *A61K 31/21* | (2006.01) |
| *A61K 9/107* | (2006.01) |
| *A61K 9/00* | (2006.01) |
| *A61K 9/06* | (2006.01) |
| *A61K 31/192* | (2006.01) |
| *A61K 9/127* | (2006.01) |
| *A61K 9/70* | (2006.01) |

(52) U.S. Cl.
CPC .............. *A61K 9/107* (2013.01); *A61K 9/0014* (2013.01); *A61K 9/06* (2013.01); *A61K 9/127* (2013.01); *A61K 9/7023* (2013.01); *A61K 31/192* (2013.01)

(58) Field of Classification Search
CPC ............................ A61K 9/7023; A61K 31/192
See application file for complete search history.

(56) References Cited

U.S. PATENT DOCUMENTS

| | | |
|---|---|---|
| 3,574,854 A | 4/1971 | Bossard |
| 3,960,782 A | 6/1976 | Daley et al. |
| 4,185,100 A | 1/1980 | Rovee et al. |
| 4,681,897 A | 7/1987 | Brand |
| 4,692,462 A | 9/1987 | Banerjee |
| 4,702,913 A | 10/1987 | Marty |
| 4,722,837 A | 2/1988 | Cameron |
| 4,732,892 A | 3/1988 | Sarpotdar et al. |
| 4,743,442 A | 5/1988 | Raaf et al. |
| 4,871,839 A | 10/1989 | Gibson |
| 4,940,456 A | 7/1990 | Sibalis et al. |
| 4,945,901 A | 8/1990 | Burcke, Jr. |
| 4,950,654 A | 8/1990 | Horn et al. |
| 4,976,952 A | 12/1990 | Lang et al. |
| 5,008,248 A | 4/1991 | Bywater et al. |
| 5,028,435 A | 7/1991 | Katz et al. |
| 5,158,761 A | 10/1992 | Kamishita et al. |
| 5,180,743 A | 1/1993 | Watanabe et al. |
| 5,210,099 A | 5/1993 | Mody et al. |
| 5,215,759 A | 6/1993 | Mausner |
| 5,217,652 A | 6/1993 | Iovanni |
| 5,217,997 A | 6/1993 | Levere et al. |
| 5,254,331 A | 10/1993 | Mausner |
| 5,256,678 A | 10/1993 | Nakaguchi |
| 5,332,758 A | 7/1994 | Nakata et al. |
| 5,391,550 A | 2/1995 | Carniglia et al. |
| 5,405,919 A | 4/1995 | Keefer et al. |
| 5,428,070 A | 6/1995 | Cooke et al. |
| 5,439,938 A | 8/1995 | Snyder et al. |
| 5,464,954 A | 11/1995 | Kimura et al. |
| 5,476,852 A | 12/1995 | Cauwenbergh |
| 5,498,420 A | 3/1996 | Edgar et al. |
| 5,505,958 A | 4/1996 | Bello et al. |
| 5,527,797 A | 6/1996 | Eisenberg et al. |
| 5,538,740 A | 7/1996 | Abad |

(Continued)

FOREIGN PATENT DOCUMENTS

| | | |
|---|---|---|
| CA | 2337772 | 1/2000 |
| CA | 2415392 A1 | 1/2002 |
| CN | 101340916 A | 1/2009 |
| DE | 10128910 A1 | 12/2002 |
| EP | 0338291 A1 | 10/1989 |
| EP | 0391342 A1 | 10/1990 |
| EP | 0 399 765 A2 | 11/1990 |
| EP | 0 424 028 A2 | 4/1991 |
| EP | 1210933 A1 | 6/2002 |
| FR | 1553063 | 11/1967 |

(Continued)

OTHER PUBLICATIONS

[No Author Listed] "Xanthan gum used in cosmetic products." Dermaxime: bio-cellular skin products. Available at http://www.dermaxime.com/xanthan.htm. Last accessed Apr. 23, 2009. 4 pages.

(Continued)

*Primary Examiner* — Gina Justice
(74) *Attorney, Agent, or Firm* — Wolf, Greenfield & Sacks, P.C.

(57) ABSTRACT

The present invention generally relates to the transdermal delivery of various compositions. In some aspects, the transdermal delivery may be facilitated by the use of a hostile biophysical environment. One set of embodiments provides a composition for topical delivery comprising ibuprofen and/or an ibuprofen salt, a nitric oxide donor, and optionally, a hostile biophysical environment. In some cases, the composition may be stabilized using a stabilization polymer such as xanthan gum, KELTROL® BT and/or KELTROL® RD; propylene glycol; and a polysorbate surfactant such as Polysorbate 20, which unexpectedly provides temperature stability to the composition, e.g., at elevated temperatures such as at least 40° C. (at least about 104° F.), as compared to compositions lacking one or more of these.

23 Claims, No Drawings

(56) References Cited

U.S. PATENT DOCUMENTS

| | | |
|---|---|---|
| 5,543,430 A | 8/1996 | Kaesemeyer |
| 5,573,776 A | 11/1996 | Harrison et al. |
| 5,575,994 A | 11/1996 | Fontanelli |
| 5,576,351 A | 11/1996 | Yoshimura et al. |
| 5,595,753 A | 1/1997 | Hechtman |
| 5,605,685 A | 2/1997 | Tseng et al. |
| 5,629,002 A | 5/1997 | Weuffen et al. |
| 5,632,981 A | 5/1997 | Saavedra et al. |
| 5,643,586 A | 7/1997 | Perricone |
| 5,645,859 A | 7/1997 | Chaudhuri et al. |
| 5,648,101 A | 7/1997 | Tawashi |
| 5,656,264 A | 8/1997 | Hanada et al. |
| 5,691,423 A | 11/1997 | Smith et al. |
| 5,698,738 A | 12/1997 | Garfield et al. |
| 5,714,472 A | 2/1998 | Gray et al. |
| 5,762,963 A | 6/1998 | Byas-Smith |
| 5,789,442 A | 8/1998 | Garfield et al. |
| 5,807,957 A | 9/1998 | Samour et al. |
| 5,824,658 A | 10/1998 | Falk et al. |
| 5,853,768 A | 12/1998 | Altadonna |
| 5,891,459 A | 4/1999 | Cooke et al. |
| 5,891,472 A | 4/1999 | Russell |
| 5,895,658 A | 4/1999 | Fossel |
| 5,906,822 A | 5/1999 | Samour et al. |
| 5,911,980 A | 6/1999 | Samour et al. |
| 5,922,332 A | 7/1999 | Fossel |
| 5,925,372 A | 7/1999 | Berner et al. |
| 5,939,094 A | 8/1999 | Durif et al. |
| 5,976,566 A | 11/1999 | Samour et al. |
| 5,985,317 A | 11/1999 | Venkateshwaran et al. |
| 6,036,977 A | 3/2000 | Drizen et al. |
| 6,103,275 A | 8/2000 | Seitz et al. |
| 6,117,872 A | 9/2000 | Maxwell et al. |
| 6,207,713 B1 | 3/2001 | Fossel |
| 6,242,229 B1 | 6/2001 | Pineau et al. |
| 6,264,979 B1 | 7/2001 | Svedman |
| 6,287,601 B1 | 9/2001 | Russell |
| 6,312,720 B1 | 11/2001 | Katinger et al. |
| 6,375,672 B1 | 4/2002 | Aksan et al. |
| 6,387,081 B1 | 5/2002 | Cooper |
| 6,444,234 B1 | 9/2002 | Kirby et al. |
| 6,448,267 B1 | 9/2002 | Anggard et al. |
| 6,451,337 B1 | 9/2002 | Smith et al. |
| 6,458,841 B2 | 10/2002 | Fossel |
| 6,468,557 B1 | 10/2002 | Lezdey et al. |
| 6,511,991 B2 | 1/2003 | Hrabie et al. |
| 6,538,033 B2 | 3/2003 | Bing |
| 6,558,695 B2 | 5/2003 | Luo et al. |
| 6,562,370 B2 | 5/2003 | Luo et al. |
| 6,565,879 B1 | 5/2003 | Luo et al. |
| 6,582,724 B2 | 6/2003 | Hsu et al. |
| 6,586,000 B2 | 7/2003 | Luo et al. |
| 6,602,912 B2 | 8/2003 | Hsu et al. |
| 6,617,337 B1 | 9/2003 | Wilcox |
| 6,642,260 B2 | 11/2003 | Haj-Yehia |
| 6,646,006 B2 | 11/2003 | Cooke et al. |
| 6,676,962 B1 | 1/2004 | Muller |
| 6,716,436 B1 | 4/2004 | Seguin |
| 6,719,997 B2 | 4/2004 | Hsu et al. |
| 6,747,063 B2 | 6/2004 | Adams et al. |
| 6,787,152 B2 | 9/2004 | Kirby et al. |
| 6,835,392 B2 | 12/2004 | Hsu et al. |
| 6,852,739 B1 | 2/2005 | Garvey et al. |
| 6,858,232 B2 | 2/2005 | Verbiscar |
| 7,241,456 B2 | 7/2007 | Vromen |
| 7,267,829 B2 | 9/2007 | Kirby et al. |
| 7,442,690 B2 | 10/2008 | Prejean et al. |
| 7,629,384 B2 | 12/2009 | Fossel |
| 7,914,814 B2 | 3/2011 | Fossel |
| 8,603,519 B2 | 12/2013 | Fossel |
| 8,604,081 B2 | 12/2013 | Fossel |
| 9,050,365 B2 | 6/2015 | Fossel |
| 9,072,659 B2 | 7/2015 | Fossel |
| 2002/0015713 A1 | 2/2002 | Murdock et al. |
| 2002/0037854 A1 | 3/2002 | Breton et al. |
| 2002/0041903 A1 | 4/2002 | Fossel |
| 2002/0168325 A1 | 11/2002 | Lerner et al. |
| 2002/0168424 A1 | 11/2002 | Shahinpoor et al. |
| 2003/0018076 A1 | 1/2003 | Fossel |
| 2003/0028169 A1 | 2/2003 | Fossel |
| 2003/0044439 A1 | 3/2003 | Dobson et al. |
| 2003/0069618 A1 | 4/2003 | Smith et al. |
| 2003/0157185 A1 | 8/2003 | Paradise |
| 2003/0203915 A1 | 10/2003 | Fang et al. |
| 2004/0082659 A1 | 4/2004 | Cooke et al. |
| 2004/0228908 A1 | 11/2004 | Liu et al. |
| 2005/0069590 A1 | 3/2005 | Buehler et al. |
| 2005/0196418 A1 | 9/2005 | Yu et al. |
| 2007/0065463 A1 | 3/2007 | Aung-Din et al. |
| 2007/0072847 A1 | 3/2007 | Mueller et al. |
| 2007/0087977 A1 | 4/2007 | Robbins |
| 2007/0105763 A1 | 5/2007 | Ghosh |
| 2007/0253911 A1 | 11/2007 | Tamarkin et al. |
| 2008/0045909 A1 | 2/2008 | Fossel |
| 2008/0233183 A1 | 9/2008 | McCook et al. |
| 2008/0280984 A1 | 11/2008 | Fossel |
| 2008/0292684 A1 | 11/2008 | Colombo et al. |
| 2009/0105336 A1 | 4/2009 | Fossel |
| 2009/0123528 A1 | 5/2009 | Fossel |
| 2009/0142390 A1 | 6/2009 | Jackson et al. |
| 2009/0221536 A1 | 9/2009 | Fossel |
| 2009/0247635 A1 | 10/2009 | Ehrenpreis |
| 2010/0196332 A1 | 8/2010 | Wichterle et al. |
| 2010/0196517 A1 | 8/2010 | Fossel |
| 2010/0280122 A1 | 11/2010 | Fossel |
| 2010/0291195 A1 | 11/2010 | Fossel |
| 2010/0291236 A1 | 11/2010 | Sadler et al. |
| 2010/0316749 A1 | 12/2010 | Fossel |
| 2010/0317737 A1 | 12/2010 | Fossel |
| 2011/0028548 A1 | 2/2011 | Fossel |
| 2011/0182977 A1 | 7/2011 | Fossel |
| 2012/0027876 A1 | 2/2012 | Ford |
| 2012/0108664 A1 | 5/2012 | Fossel |
| 2012/0148665 A1 | 6/2012 | Fossel |
| 2012/0258865 A1 | 10/2012 | Short et al. |
| 2013/0072498 A1 | 3/2013 | Fossel |
| 2013/0289059 A1 | 10/2013 | Fossel |
| 2014/0004176 A1 | 1/2014 | Fossel |
| 2014/0004177 A1 | 1/2014 | Fossel |
| 2014/0010866 A1 | 1/2014 | Fossel |
| 2014/0038205 A1 | 2/2014 | Raynard |
| 2014/0044774 A1 | 2/2014 | Fossel |
| 2014/0051707 A1 | 2/2014 | Fossel |
| 2014/0051717 A1 | 2/2014 | Fossel |
| 2014/0066452 A1 | 3/2014 | Fossel |
| 2014/0066511 A1 | 3/2014 | Fossel |
| 2014/0072618 A1 | 3/2014 | Fossel |
| 2014/0073697 A1 | 3/2014 | Fossel |
| 2014/0086980 A1 | 3/2014 | Fossel |
| 2015/0010619 A1 | 1/2015 | Fossel |
| 2015/0011570 A1 | 1/2015 | Fossel |
| 2015/0080470 A1 | 3/2015 | Fossel |

FOREIGN PATENT DOCUMENTS

| | | |
|---|---|---|
| FR | 5940 | 4/1968 |
| FR | 2602678 | 2/1988 |
| FR | 2740453 | 4/1997 |
| FR | 2810540 | 12/2001 |
| GB | 2094142 A1 | 9/1982 |
| GB | 2126868 A | 4/1984 |
| JP | 57-053404 A | 3/1982 |
| JP | 60-252412 A | 12/1985 |
| JP | 03-093707 | 4/1991 |
| JP | 04-005231 | 9/1992 |
| JP | 05-279250 A | 10/1993 |
| JP | 6-247832 | 9/1994 |
| JP | 6-287135 A | 10/1994 |
| JP | 7-53336 | 2/1995 |
| JP | 07-316075 A | 12/1995 |
| JP | 09-143098 A | 6/1997 |
| JP | 9-208460 A | 8/1997 |
| JP | 9-241156 A | 9/1997 |
| JP | 10-167953 | 6/1998 |

(56) References Cited

FOREIGN PATENT DOCUMENTS

| | | |
|---|---|---|
| JP | 2000-186028 A | 7/2000 |
| JP | 2001-288068 A | 10/2001 |
| JP | 2002-003373 A | 1/2002 |
| JP | 2003-286129 A | 10/2003 |
| JP | 2004-059439 A | 2/2004 |
| JP | 2005-200370 A | 7/2005 |
| RU | 2212232 C2 | 9/2003 |
| RU | 2229286 C2 | 5/2004 |
| WO | WO 88/06034 A1 | 8/1988 |
| WO | WO 92/08705 | 5/1992 |
| WO | WO 92/15276 A2 | 9/1992 |
| WO | WO 94/09750 A1 | 5/1994 |
| WO | WO 95/13060 | 5/1995 |
| WO | WO 95/15147 | 6/1995 |
| WO | WO 95/15147 A1 | 6/1995 |
| WO | WO 96/08966 A1 | 9/1995 |
| WO | WO 96/14748 | 5/1996 |
| WO | WO 96/29988 A1 | 10/1996 |
| WO | WO 97/10830 A1 | 3/1997 |
| WO | WO 97/16983 A1 | 5/1997 |
| WO | WO 97/39760 A1 | 10/1997 |
| WO | WO 99/13717 A1 | 3/1999 |
| WO | WO 00/03689 A2 | 1/2000 |
| WO | WO 00/40215 A1 | 7/2000 |
| WO | WO 00/54773 A1 | 9/2000 |
| WO | WO 00/69469 A1 | 11/2000 |
| WO | WO 01/45713 A1 | 6/2001 |
| WO | WO 03/049593 A2 | 6/2003 |
| WO | WO 03/072039 A2 | 9/2003 |
| WO | WO 03/078437 A1 | 9/2003 |
| WO | WO 03/080104 A2 | 10/2003 |
| WO | WO 2005/081964 A2 | 9/2005 |
| WO | WO 2005/102282 A1 | 11/2005 |
| WO | WO 2005/102307 A2 | 11/2005 |
| WO | WO 2006/096360 A1 | 9/2006 |
| WO | WO 2008/076287 A2 | 6/2008 |
| WO | WO 2010/151240 A1 | 12/2010 |
| WO | WO 2012/092528 A1 | 7/2012 |

OTHER PUBLICATIONS

[No Author Listed] "Xanthan gum." Wikipedia. Available at http://en.wikipedia.org/wiki/Xanthan. Last accessed Apr. 13, 2009. 3 pages.
[No Author Listed] BioSpace Press Release Transdermal Ibuprofen development Complete: NDA to Be Filed (web page) http://biospace.com/news_story.aspx?NewsEntityId=18470820. Published Dec. 16, 2004. 2 pages.
[No Author Listed] Peripheral Vascular Disease—Wikipedia (web page) http://en.wikipedia.org/wiki/Peripheral_vascular_disease [Jan. 18, 2010]. 5 pages.
[No Author Listed] Peripheral Vascular Disease (web page) http://www.americanheart.org/presenter.jhtml?identifier=4692 [Jan. 18, 2010]. 2 pages.
[No Author Listed] Sex and Sexuality Orgasm Information. Extended Orgasm. Unknown date. 7 pages.
Argiolas, Nitric Oxide is a Central Mediator of Penile Erection. Neuropharmacology, vol. 33, No. 11, pp. 1339-1344 (1994).
Bessatsu, Igaku no Ayumi, Shinkei Shikkan (A Separate Volume: Progress in Medicine, Neurological Desiases), 1999:314-6. Chinese.
Biagini et al., [Intermittent claudication: topical treatment with isosorbide dinitrate ointment. Preliminary results]. G Ital Cardiol. 1981;11(7):514-521.
Birder et al., Adrenergic and capasaicin evoked nitric oxide release from urothelium and afferent nerves in urinary bladder. American Journal of Physiology, vol. 275, pp. F226-F229 (1998). [Abstract only].
Boger et al., Restoring vascular nitric oxide formation by L-arginine improves the symptoms of intermittent claudication in patients with peripheral arterial occlusive disease. J Am Coll Cardiol. Nov. 1998;32(5):1336-44.
Bunker, C.B., et al., "Alterations in scalp blood flow after the epicutaneous application of 3% minoxidil and 0.1% hexyl nicotinate in alopecia," Correspondence, pp. 668-669 (1986).
Cooper, et al., "Transdermal Delivery of Drugs," CRC Press, vol. II, pp. 57-62 (1987).
De Boer, E.M., et al., "Does Topical Minoxidil Increase Skin Blood Flow?", Acta Derm Venereol, vol. 68, pp. 271-274 (1988).
Dietz, et al., "Is nitric oxide involved in cutaneous vasodilation during body heating in humans?" J. Appl. Physiol, vol. 76, No. 5, pp. 2047-2053 (1994).
Extended Europrean Search Report for EP 09014985.7 mailed Apr. 22, 2010.
Extended European Search Report for EP 11182318.3 mailed Jan. 20, 2012.
Extended European Search Report for EP 13167916.9 mailed Jul. 30, 2013.
Extended European Search Report for EP 11173316.8 mailed Sep. 22, 2011.
Extended European Search Report for EP 11174380.3 mailed Jan. 13, 2012.
Extended European Search Report for EP 11174375.3 mailed Jan. 13, 2012.
Flick, Cosmetics Additives: An Industrial Guide. Noyes Publications, Park Ridge, New Jersey, U.S.A. 1991: 790.
Fossel, Improvement of Temperature and Flow in Feet of Subjects with Diabetes With Use of a Transdermal Preparation of L-Arginine. Diabetes Care, vol. 27, No. 1, Jan. 2004, pp. 284-285.
Garban et al., Effect of aging on nitric oxide-mediated penile erection in rats. Am. J. Physiol., H467-H475 (1995).
Goldenberg, The Care of the Diabetic Foot. Judy Dan Research & Treatment Centre. Available at http://www.ontariowoundcare.com/footcarephysician.htm. Last accessed Sep. 20, 2010. 9 pages.
Gutman et al., Molecular discovery of transdermal delivery nanotechnology from computer experiments and experimental R & D. Strategic Science Technologies. Presented at the Langer USA—Japan Drug Delivery Conference. Maui, Hawaii. Dec. 2011. 21 pgs.
Haldiya et al., Dermal Ulcers and Hypertension in Salt Workers. Current Science, vol. 87, No. 8, Oct. 25, 2004, pp. 1139-1141.
Hirsch et al., Peripheral Arterial Disease Detection, Awareness, and Treatment in Primary Care. J Am Med Assoc. 2001;286(11):1317-1324.
Hirvonen et al. Effect of diffusion potential, osmosis and ion-exchange on transdermal drug delivery: theory and experiments. Jornal of Controlled Release 56 (1998) 33-39.
Hwang et al., Evaluation of Vasculogenic Impotence Using Dynamic Penile Washout Test. J. Formosan Med. Assoc., vol. 89, No. 11, pp. 992-996 (1990).
International Preliminary Examination Report for PCT/US98/19429 mailed Apr. 6, 2000.
International Search Report for International Application No. PCT/US98/19429, mailed Jan. 11, 1999.
International Preliminary Report on Patentability for PCT/US2005/005726 mailed Sep. 8, 2006.
International Search Report and Written Opinion for PCT/US05/05726 mailed Sep. 19, 2005.
International Preliminary Report on Patentability for PCT/US2005/013228 mailed Nov. 2, 2006.
International Search Report and Written Opinion for PCT/US05/13228 mailed Jul. 15, 2005.
International Preliminary Report on Patentability for PCT/US2005/013230 mailed Nov. 2, 2006.
International Search Report and Written Opinion for PCT/US05/13230 mailed Oct. 28, 2005.
International Preliminary Report on Patentability for PCT/US2009/003750 mailed Jan. 12, 2012.
International Search Report and Written Opinion for PCT/US2009/003750 mailed May 19, 2010.
International Preliminary Report on Patentability for PCT/US2009/003749 mailed Jan. 12, 2012.
International Search Report and Written Opinion for PCT/US2009/003749 mailed May 19, 2010.
International Preliminary Report on Patentability for PCT/US2011/067993 mailed Jul. 11, 2013.
International Search Report and Written Opinion for PCT/US2011/067993 mailed May 1, 2012.
International Preliminary Report on Patentability for PCT/US2011/067987 mailed Jul. 11, 2013.
International Search Report and Written Opinion for PCT/US2011/067987 mailed Apr. 30, 2012.

(56) References Cited

OTHER PUBLICATIONS

International Preliminary Report on Patentability for PCT/US2011/067991 mailed Jul. 11, 2013.
International Search Report and Written Opinion for PCT/US2011/067991 mailed Apr. 30, 2012.
International Preliminary Report on Patentability for PCT/US2011/067992 mailed Jul. 11, 2013.
International Search Report and Written Opinion for PCT/US2011/067992 mailed Apr. 30, 2012.
International Preliminary Report on Patentability for PCT/US2011/067990 mailed Jul. 11, 2013.
International Search Report and Written Opinion for PCT/US2011/067990 mailed Apr. 30, 2012.
Japanese Office Action for Application No. 2011-93358 mailed Nov. 1, 2012.
Japanese Office Action for Application No. 2011-283904 mailed Jul. 10, 2013.
Katzbauer, Properties and applications of xanthan gum. Polymer Degradation and Stability. 1998;59(1-3): 81-4.
Kirkeby et al., Role of the L-arginine/nitric oxide pathway in relaxation of isolated human penile cavernous tissue and circumflex veins. Acta Physiol Scand., vol. 149, pp. 385-392 (1993).
Klemp et al., Subcutaneous Blood Flow in Early Male Pattern Baldness. J. Invest. Dermatol., 92, pp. 725-726 (1989).
Laan et al., Assessment of female sexual arousal: Response specificity and construct validity. Psychophysiology, vol. 32, pp. 476-485 (1995).
Mathias et al., Topical Capsaicin for Chronic Neck Pain. Am. J. Phys. Rehabil., vol. 74, pp. 39-44 (1995).
Matuszak et al., Thermodynamic Driving Force for Molecular Diffusion—Lattice Density Functional Theory Predictions. J. Non-Equilib. Thermodym. 2006, vol. 31, No. 4, pp. 355-384.
McLatchie et al., The effects of pH on the interaction between capsaicin and the vanilloid receptor in rat dorsal root ganglia neurons. Br J Pharmacol. Feb. 2001;132(4):899-908.
Moody et al., Effects of long-term oral administration of L-arginine on the rat erectile response. The Journal of Urology. 1997;158:942-947.
Nakaki et al., Beneficial Circulatory Effect of L-Arginine. Jpn. J. Pharmacol. 66, 167-171 (1994).
Napoli et al., Nitric oxide-releasing drugs. Annu Rev Pharmacol Toxicol. 2003;43:97-123. Epub Jan. 10, 2002.
Owen et al., Topical nitroglycern: A potential treatment for impotence. The Journal of Urology. 1989;143:546-548. Abstract.
Pauly et al., Liposomes containing amino acids and peptides and proteins for skin care. Chemical abstracts, 1998, 113:65069 (Abstract).
Riedel et al., Different mechanisms of L-Arginine induced dilation of brain arterioles in normotensive and hypertensive rats. Brain Res. 1995;671(1):21-6. CA: 122 (11) 130053t [Abstract only].
Rinshyo, Treatment and prevention of diabetic foot ulcer. Shin Jidai no Tonyobyogaku (Studies on Diabetes in a New Age). 2002;4:354-8. Chinese.
Scholermann et al., Clinical and biophysical efficacy of a novel body cream (Eucerin® amino body cream) for aged dry skin containing urea and L-arginine. J Euro Acad Dermatol Venereol. 1998; 11:S270. Abstract P363.
Schölermann et al., Clinical and biophysical efficacy of a novel coenzyme $Q_{10}$ containing anit-wrinkle cream (Eucerin® Q10 active). J EP Acad Dermatol Venereol, 11: S270, year unknown.
Shukla et al., Nitric oxide inhibits wounds collagen synthesis. Mol Cell Biochem. Oct. 1999;200(1-2):27-33.
Singh et al., Response of digital arteries to endothelium dependent and independent vasodilators in patients with Raynaud's phenomenon. European Journal of Clinical Investigation. 1995; 25:182-185.
Singh, Xantham Gum. Printed from: Pharmaceutical Excipients. London: Pharmaceutical Press. 2006. Electronic version. Last revision Aug. 7, 2005. 6 pages.
Sonntag et al., Role of nitric oxide in local blood flow control in the anaesthetized dog. European Journal of Physiology. 1992:194-199.
Suhonen et al., Epidermal cell culture model derived from rat keratinocytes with permeability characteristics comparable to human cadaver skin. Euorpean Journal of Pharmaceutical Sciences 20 (2003) 107-113.
Supplementary European Search Report for EP 98946099.3 mailed Mar. 1, 2006.
Supplementary European Search Report for EP 05723558.2 mailed Feb. 17, 2009.
Supplementary European Search Report for EP 05737763.2 mailed May 12, 2009.
Supplementary European Search Report for EP 05737752.5 mailed Apr. 21, 2009.
The Merck Index, An Encyclopedia of Chemicals, Drugs, and Biologicals, Twelfth Edition, p. 817.
Thompson, Part IV. Exercise as Adjunctive Therapy for Patients with Vascular Disease. Definition and Classification of Peripheral Arterial Disease. In: Exercise & Sports Cardiology. 2001: 372.
Tiso et al., Oral versus topical ibuprofen for chronic knee pain: A prospective randomized pilot study. Pain Physician. Sep./Oct. 2010;13:457-467.
Tseng et al., Increase of nitric oxide production by L-arginine potentiates i.c.v. administered—endorphin-induced antinociception in the mouse. European Journal of Pharmacology. 1992;212:301-303.
Wang et al., Nitric oxide mediates penile erection in cats. The Journal of Urology. 1994;151:234-237.
Whitmore et al., Acute effect of topical minoxidil on digital blood flow in patients with raynaud's phenomenon. The Journal of Rheumatology. 1995;22(1):50-54.
Writtion Opinion for PCT/US98/19429 mailed Jul. 14, 1999.
Yasuda, The role of nitric oxide in the pathophysiology of diabetic neuropathy. The Autonomic Nervous System. 2003;40:285-289.
[No Author Listed] MoonDragon's Health & Wellness: Nutrition Basics: Amino Acids-Arginine. Available at http://www.moondragon.org/health/nutritionbasics/aminoacids/arginine.html. Last accessed Jun. 23, 2014. 8 pages.
International Search Report and Written Opinion for PCT/US2014/027277 mailed Jul. 3, 2014.
Sauermann et al., Caplus Copyright. AN 1995: 648333, abstract WO 9515147, Jul. 1995.
[No Author Listed] BASF Pharma Ingredients and Services, Ibuprofen Technical Information. Apr. 2010. p. 11.
Hyldahl et al., Effects of ibuprofen topical gel on muscle soreness. Med Sci Sports Exerc. Mar. 2010;42(3):614-21.
Lin et al., Efficacy of topical non-steroidal anti-inflammatory drugs in the treatment of osteoarthritis: meta-analysis of randomised controlled trials. BMJ. Aug. 7, 2004;329(7461):324. Epub Jul. 30, 2004.
Trnavský et al., Efficacy and safety of 5% ibuprofen cream treatment in knee steoarthritis. Results of a randomized, double-blind, placebo-controlled study. J Rheumatol. Mar. 2004;31(3):565-72.
Whitefield et al., Comparative efficacy of a proprietary topical ibuprofen gel and oral ibuprofen in acute soft tissue injuries: a randomized, double-blind study. J Clin Pharm Ther. Dec. 2002;27(6):409-17.
Extended European Search Report for EP 11852275.4 mailed Dec. 9, 2014.
Extended European Search Report for EP 11854321.4 mailed Dec. 8, 2014.
Extended European Search Report for EP 11853771.1 mailed Dec. 11, 2014.
Extended European Search Report for EP 11853913.9 mailed Dec. 5, 2014.
Extended European Search Report for EP 11854161.4 mailed Dec. 9, 2014.
Flick, Cosmetic and toiletry formulations. $2^{nd}$ ed., Noyes Publications, Park Ridge, NJ, 1989, vol. 1, pp. 234, 237.
Griffith et al., A multicentered study of lysine therapy in Herpes simplex infection. Dermatologica. 1978;156(5):257-67. Abstract Only.
Griffith et al., Relation of arginine-lysine antagonism to herpes simplex growth in tissue culture. Chemotherapy. 1981;27(3):209-13. Abstract Only.
Naito et al., Antiviral effect of arginine against herpes simplex virus type 1. Int J Mol Med. Apr. 2009;23(4):495-9.

DELIVERY OF IBUPROFEN AND OTHER COMPOUNDS

RELATED APPLICATIONS

This application is a continuation of U.S. patent application Ser. No. 12/812,187, having a §371(c) date of Mar. 28, 2011, entitled "Topical Compositions Containing Ibuprofen," by E. T. Fossel, which is a national stage filing under 35 U.S.C. §371 of International Application No. PCT/US2009/003749, filed Jun. 24, 2009, entitled "Topical Compositions Containing Ibuprofen," by Eric T. Fossel. The contents of each of these applications are incorporated herein by reference in their entireties for all purposes.

FIELD OF INVENTION

The present invention generally relates to the transdermal delivery of compositions.

BACKGROUND

Local transdermal delivery of drugs, while desirable, is limited by current technologies. Few pharmaceutical entities have successfully been delivered transdermally in effective dosages. For example, a limited number of drugs, such as steroids, nicotine, and nitroglycerine, which are non-charged and do not form hydrogen bonds, have been successfully delivered by passive diffusion, relying on the concentration gradient between outside and inside the skin to deliver the drug in accordance with Fick's first law of diffusion. The amount of pharmaceutical agent that can be delivered through simple diffusion is also limited. For instance, once the concentration inside the stratum corneum becomes equal to that outside, flow of pharmaceutical agent may stop. Thus, improvements in the transdermal delivery of compositions, locally or systemically, are needed.

SUMMARY OF THE INVENTION

The present invention generally relates to the transdermal delivery of compositions, locally or systemically, and in some embodiments, to the transdermal delivery of compositions by a hostile biophysical environment. Examples include ibuprofen or other pharmaceutical agents. The subject matter of the present invention involves, in some cases, interrelated products, alternative solutions to a particular problem, and/or a plurality of different uses of one or more systems and/or articles.

In one set of embodiments, compositions having relatively high temperature stability are provided. In some embodiments, for instance, a composition of the present invention may include a stabilization polymer, propylene glycol, and a polysorbate surfactant. Non-limiting examples of stabilization polymers include xanthan gum, KELTROL® BT and/or KELTROL® RD; an example of a polysorbate surfactant is Polysorbate 20. Such a combination of components to create high temperature stability are surprising, since compositions involving any two of these components (but not the third) were found to lack such high temperature stabilization properties. It is not currently known why this combination of components is remarkably effective at facilitating relatively high temperature stability of the compositions discussed herein, as these components are not known to participate in any significant chemical reactions with each other, and high temperature stability is greatly reduced when one of the components is removed. In addition, propylene glycol is not known to work in pharmaceutical compositions as a stabilizing agent.

Thus, in one aspect, the present invention is directed to a composition for topical delivery to the skin of a subject. In one set of embodiments, the composition includes a nitric oxide donor, a hostile biophysical environment, a stabilization polymer, propylene glycol, a polysorbate surfactant, and ibuprofen and/or a ibuprofen salt.

In another set of embodiments, at least about 80% by weight of the composition comprises water, at least one chloride salt, a nitric oxide donor, a stabilization polymer, propylene glycol, a polysorbate surfactant, and ibuprofen and/or a ibuprofen salt.

The composition, in yet another set of embodiments, includes water, sodium chloride, a nitric oxide donor, glyceryl stearate, cetyl alcohol, potassium chloride, squalane, a stabilization polymer, isopropyl myristate, oleic acid, propylene glycol, a polysorbate surfactant, and ibuprofen and/or a ibuprofen salt.

The composition, in still another set of embodiments, includes each of the following compounds at concentrations of no more than ±20% of the stated concentrations: water at a concentration of about 44.2% weight, sodium chloride at a concentration of about 10% weight, a nitric oxide donor at a concentration of about 7.5% weight, glyceryl stearate at a concentration of about 7% weight, cetyl alcohol at a concentration of about 7% weight, potassium chloride at a concentration of about 5.5% weight, propylene glycol at a concentration of about 5% weight, squalane at a concentration of about 4% weight, a polysorbate surfactant at a concentration of about 2% by weight, and isopropyl myristate at a concentration of about 1% weight, oleic acid at a concentration of about 1% weight, a stabilization polymer at a concentration of about 0.8% weight, ibuprofen and/or a ibuprofen salt at a concentration of about 5.0% weight.

The composition, in another set of embodiments, includes a nitric oxide donor, a hostile biophysical environment, a stabilization polymer, propylene glycol, a polysorbate surfactant and ibuprofen and/or a ibuprofen salt. In still another set of embodiments, the composition includes a stabilization polymer, propylene glycol, a polysorbate surfactant, and ibuprofen and/or a ibuprofen salt. In another set of embodiments, at least about 80% by weight of the composition comprises water, at least one chloride salt, a stabilization polymer, propylene glycol, a polysorbate surfactant, and ibuprofen and/or a ibuprofen salt.

In another aspect, the present invention is directed to the use of a composition in the preparation of a medicament for treatment of a disease or condition as discussed herein. In one set of embodiments, the composition for the medicament comprises a nitric oxide donor, a hostile biophysical environment, a stabilization polymer, propylene glycol, a polysorbate surfactant, and ibuprofen and/or a ibuprofen salt.

In another set of embodiments, at least about 80% by weight of the composition for the medicament comprises water, at least one chloride salt, a nitric oxide donor, a stabilization polymer, propylene glycol, a polysorbate surfactant, and ibuprofen and/or a ibuprofen salt.

The composition for the medicament, in yet another set of embodiments, includes water, sodium chloride, a nitric oxide donor, glyceryl stearate, cetyl alcohol, potassium chloride, squalane, a stabilization polymer, isopropyl myristate, oleic acid, propylene glycol, a polysorbate surfactant, and ibuprofen and/or a ibuprofen salt.

The composition for the medicament, in still another set of embodiments, includes each of the following compounds at concentrations of no more than ±20% of the stated concentrations: water at a concentration of about 44.2% weight, sodium chloride at a concentration of about 10% weight, a nitric oxide donor at a concentration of about 7.5% weight, glyceryl stearate at a concentration of about 7% weight, cetyl alcohol at a concentration of about 7% weight, potassium chloride at a concentration of about 5.5% weight, propylene glycol at a concentration of about 5% weight, squalane at a concentration of about 4% weight, a polysorbate surfactant at a concentration of about 2% by weight, and isopropyl myristate at a concentration of about 1% weight, oleic acid at a concentration of about 1% weight, a stabilization polymer at a concentration of about 0.8% weight, ibuprofen and/or a ibuprofen salt at a concentration of about 5.0% weight.

The composition for the medicament, in another set of embodiments, includes a nitric oxide donor, a hostile biophysical environment, a stabilization polymer, propylene glycol, a polysorbate surfactant and ibuprofen and/or a ibuprofen salt. In still another set of embodiments, the composition for the medicament includes a stabilization polymer, propylene glycol, a polysorbate surfactant, and ibuprofen and/or a ibuprofen salt. In another set of embodiments, at least about 80% by weight of the composition for the medicament comprises water, at least one chloride salt, a stabilization polymer, propylene glycol, a polysorbate surfactant, and ibuprofen and/or a ibuprofen salt.

The present invention, in another aspect, is directed to a method of making one or more of the embodiments described herein. In yet another aspect, the present invention is directed to a method of using one or more of the embodiments described herein. In still another aspect, the present invention is directed to a method of promoting one or more of the embodiments described herein.

Other advantages and novel features of the present invention will become apparent from the following detailed description of various non-limiting embodiments of the invention. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

DETAILED DESCRIPTION

The present invention generally relates to the transdermal delivery of various compositions. In some aspects, transdermal delivery may be facilitated by the use of a hostile biophysical environment. One set of embodiments provides a composition for topical delivery comprising ibuprofen and/or an ibuprofen salt, and optionally, a hostile biophysical environment and/or a nitric oxide donor. In some cases, the composition may be stabilized using a combination of a stabilization polymer (such as xanthan gum, KELTROL® BT and/or KELTROL® RD), propylene glycol, and a polysorbate surfactant such as Polysorbate 20, which combination unexpectedly provides temperature stability to the composition, e.g., at elevated temperatures such as at least 40° C. (at least about 104° F.), as compared to compositions lacking one or more of these.

One aspect of the invention provides compositions for the topical delivery of substances such as pharmaceutical agents (e.g., drugs, biological compounds, etc.). The pharmaceutical agents may be applied to the skin of a subject, e.g. a human, to aid in treatment of medical conditions or diseases, and/or the symptoms associated thereof. In some embodiments, the invention provides for the treatment of medical conditions or diseases and/or ailments using pharmaceutical agents (for example, to treat a subject diagnosed with a medical condition or disease, as described herein), and in some cases, the invention provides for the delivery of a minimum amount of pharmaceutical agents to provide effective levels of medication to an effected area topically while limiting side effects. In some cases, the effective dosage of the pharmaceutical agent may be lower than the effective dosage of the pharmaceutical agent when taken orally.

For example, in one set of embodiments, the pharmaceutical agent is ibuprofen and/or an ibuprofen salt. While ibuprofen is an effective agent against pain when orally administered, it can be irritating to the lining of the stomach, and people with a tendency to develop ulcers or have an irritated upper gastrointestinal track are typically warned to avoid the use of ibuprofen. The present invention thus allows, in one set of embodiments, the topical application of ibuprofen to a site of inflammation or pain, while avoiding the rest of the body, especially the stomach. The composition may also include a nitric oxide donor such as L-arginine, which may be useful, for example, to increase localized blood flow at the site of delivery, which in turn can enhance delivery of the pharmaceutical agent, e.g., locally or systemically. In some cases, the enhancement may occur by maintaining an appropriate concentration gradient at the site of delivery.

In addition, in some cases, the composition may be formulated such that it creates a hostile biophysical environment to a pharmaceutical agent (e.g., to ibuprofen). In a hostile biophysical environment, the environment surrounding the pharmaceutical agent may be such that the pharmaceutical agent is in a chemically and/or energetically unfavorable environment, relative to the skin (e.g., the chemical potential and/or the free energy of the pharmaceutical agent within the hostile biophysical environment is significantly greater than the chemical potential and/or the free energy of the pharmaceutical agent within the skin, thus energetically favoring transport into the skin), especially the stratum corneum.

Examples of such compositions are discussed in International Patent Application No. PCT/US2005/013228, filed Apr. 19, 2005, entitled "Transdermal Delivery of Beneficial Substances Effected by a Hostile Biophysical Environment," by E. Fossel, published as WO 2005/102282 on Nov. 3, 2005, incorporated herein by reference. Other techniques for hostile biophysical environments are discussed in detail herein. However, such compositions often are not stable at relatively high temperatures, e.g., at elevated temperatures such as at least 40° C. (at least about 104° F.) for periods of time of at least about a day. Thus, in one set of embodiments, compositions having relatively high temperature stability are provided herein. In some embodiments, for instance, a composition of the present invention may further include a stabilization polymer, propylene glycol, and a polysorbate surfactant. Non-limiting examples of stabilization polymers include xanthan gum, KELTROL® BT and/or KELTROL® RD; an example of a polysorbate surfactant is Polysorbate 20. Additional examples are discussed herein.

Such a combination of components to create high temperature stability are surprising, since compositions involving any two of these components (but not the third) were found to lack such high temperature stabilization properties. It is not currently known why this combination of components is remarkably effective at facilitating relatively high temperature stability of the compositions discussed herein, as these components are not known to participate in any significant chemical reactions with each other, and high temperature stability is greatly reduced when one of the components is removed. In addition, propylene glycol is not known to work in pharmaceutical compositions as a stabilizing agent.

For instance, in one set of embodiments, a composition may be determined to be one that has high temperature stability by determining whether the composition exhibits phase separation over a relatively long period of time, e.g., over at least an hour, at least about 2 hours, at least a day, at least about a week, at least about 4 weeks, etc. For example, in some embodiments, a composition is exposed to ambient temperature and pressure for at least 1 hour, and the composition is then analyzed to determine whether the composition exhibits phase separation or a change in phase. A stable compound is one that exhibits no phase separation, whereas an unstable compound may exhibit phase separation. Such stability may be useful, for example, for storage of the composition, transport of the composition, shelf life, or the like.

The pharmaceutical agent (e.g., ibuprofen and/or an ibuprofen salt) may be present at any suitable concentration. For instance, in some cases, the pharmaceutical agent may be present at a concentration of at least about 1%, at least about 2%, at least about 3%, at least about 4%, at least about 5%, at least about 6%, at least about 7%, at least about 7.5%, at least about 8%, at least about 9%, or at least about 10% by weight of the composition. In addition, the pharmaceutical agent may be present in native form and/or as a salt. For example, if ibuprofen is present, it may be used in its native form, and/or as one or more ibuprofen salts, e.g., the sodium salt of ibuprofen, the potassium salt of ibuprofen, the lysine salt of ibuprofen, the arginine salt of ibuprofen, etc. Ibuprofen is readily commercially available.

As used herein, a "stabilization polymer" is a polymer that comprises xanthan gum, a xanthan gum derivative, and/or a xanthan gum equivalent, for example, KELTROL® BT and/or KELTROL® RD, KELZAN® XC, KELZAN® XCD, KELZAN® D, KELZAN® CC, XANTURAL® 180, XANTURAL® 75, or the like, all of which can be obtained commercially from various suppliers. In some embodiments, combinations of these and/or other polymers are also possible. In some cases, the stabilization polymer is chosen to be one which is at least generally regarded as safe for use in humans. In addition, in certain embodiments, the stabilization polymer is produced synthetically, and/or one which has been purified to some degree. The stabilization polymer may have any suitable molecular weight, for example, at least about 1 million, at least about 2 million, at least about 5 million, at least about 10 million, at least about 25 million, or at least about 50 million.

The stabilization polymer may be present at any suitable concentration within the composition. For example, the stabilization polymer may be present at a concentration of at least about 0.1%, at least about 0.2%, at least about 0.3%, at least about 0.4%, at least about 0.5%, at least about 0.6%, at least about 0.7%, at least about 0.8%, at least about 0.9%, or at least about 1% by weight of the composition. In some cases, more than one stabilization polymer may be present, and each stabilization polymer may be present in any suitable amount. As a specific example, in certain embodiments, the stabilization polymer consists essentially of KELTROL® BT and/or KELTROL® RD. In certain instances, the stabilization polymer may have a fixed ratio of KELTROL® BT and/or KELTROL® RD, for example, 1:1 or 3:5 by weight. In another example, the KELTROL® BT may be present at a concentration of about 0.3% by weight and the KELTROL® RD may be present at a concentration of 0.5% by weight of the composition, or one or both of these may be present at one of the other concentrations described above. Combinations of these and/or other stabilization polymers are also contemplated in other embodiments, e.g., KELTROL® BT and xanthan gum, KELTROL® RD and xanthan gum, etc. In some cases, thickening agents can be used instead of, or in conjunction with a stabilization polymer. Many thickening agents can be obtained commercially. Thickening agents include those used in the food industry, or are GRAS agents (generally regarded as safe), e.g., alginin, guar gum, locust bean gum, collagen, egg white, furcellaran, gelatin, agar, and/or carrageenan, as well as combinations of these and/or other stabilization polymers. It should thus be appreciated that, in the specification herein, references to stabilization polymers, in other embodiments, should be understood to also include thickening agents in conjunction or instead of stabilization polymers, Propylene glycol can be obtained commercially, and can be present as any stereoisomer or racemic mixture of isomers. It may also be present at any suitable concentration. For instance, propylene glycol may be present at a concentration of at least about 1%, at least about 2%, at least about 3%, at least about 4%, at least about 5%, at least about 6%, at least about 7%, at least about 8%, at least about 9%, or at least about 10% by weight of the composition. In some cases, other glycols can be used in conjunction or instead of propylene glycol, such as butylene glycol. Accordingly, it should thus be appreciated that, in the specification herein, references to propylene glycol, in other embodiments, should be understood to also include other glycols in conjunction or instead of propylene glycol.

In addition, a polysorbate surfactant can also be present any suitable concentration within the composition. For instance, in some cases, the polysorbate surfactant may be present at a concentration of at least about 1%, at least about 2%, at least about 3%, at least about 4%, at least about 5%, at least about 6%, at least about 7%, at least about 8%, at least about 9%, or at least about 10% by weight of the composition. A "polysorbate surfactant," as used herein, is a surfactant comprising a polysorbate. For example, the surfactant may comprise sorbitan monolaurate, sorbitan monopalmitate, sorbitan monostearate, sorbitan monooleate, or another sorbitan salt. In some cases, the polysorbate surfactant has a molecular formula:

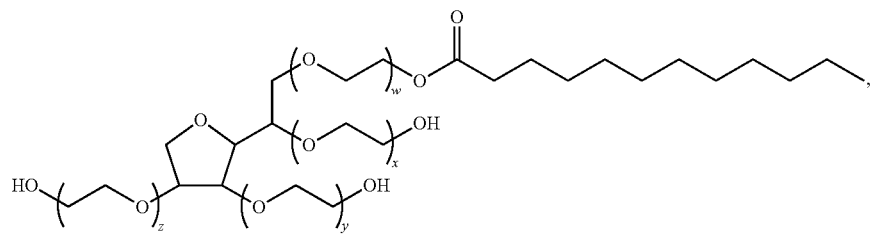

where w, x, y, and z are any suitable positive integers. w, x, y, and z may also each be independently the same or different. In one set of embodiments, w+x+y+z is 20 (e.g., as in Polysorbate 20). In some cases, other polymeric sugars can be used instead of, or in conjunction with, a polysorbate surfactant. Thus, it should be appreciated that, in the specification herein, references to a polysorbate surfactant are by way of example, and in other embodiments, it should be understood that references to a polysorbate surfactant may include other polymeric sugars in conjunction or instead of a polysorbate surfactant.

In some cases, the composition may have a fixed ratio of the stabilization polymer to propylene glycol to the polysorbate surfactant. For instance, the ratio of these may be about 1:1:1, about 1:6:3, about 1:6:2, about 1:7:2, about 1:7:3, about 1.5:1:1, about 1.5:6:3, about 1.5:6:4, about 1:6:2.5, about 1:6.25:2.5, about 1:6.25:2.5, etc. As mentioned above, such ratios may be useful, in certain embodiments of the invention, in providing temperature stability to the composition.

As discussed, the composition may also comprise a nitric oxide donor, for example, L-arginine and/or L-arginine hydrochloride. In some cases, such a nitric oxide donor may be used to increase localized blood flow at the site where the composition is applied, which may enhance delivery of the pharmaceutical agent. The nitric oxide donor may be present at any suitable concentration within the composition. For instance, in some cases, the nitric oxide donor is present at a concentration of at least about 1%, at least about 2%, at least about 3%, at least about 4%, at least about 5%, at least about 6%, at least about 7%, at least about 7.5%, at least about 8%, at least about 9%, or at least about 10% by weight of the composition. In some cases, one or more nitric oxide donors (e.g., 2, 3, 4, 5, 6, 7, 8, 9, 10, etc. nitric oxide donors) may be used.

A "nitric oxide donor," as used herein, is a compound that is able to release nitric oxide and/or chemically transfer the nitric oxide moiety to another molecule, directly or indirectly, for example, through a biological process. The nitric oxide donor may release nitric oxide into the skin, and/or tissues such as muscles and/or elements of the circulatory system in close proximity to the surface of the skin. Non-limiting examples of nitric oxide donors include arginine (e.g., L-arginine and/or D-arginine), arginine derivatives (e.g., L-arginine hydrochloride and/or D-arginine hydrochloride), nitroglycerin, polysaccharide-bound nitric oxide-nucleophile adducts, N-nitroso-N-substituted hydroxylamines, 1,3-(nitrooxymethyl)phenyl-2-hydroxybenzoate, etc., and/or any combination of these and/or other compounds.

Besides L-arginine and L-arginine hydrochloride, other non-limiting examples of nitric oxide donors include D,L-arginine, D-arginine, or alkyl (e.g., ethyl, methyl, propyl, isopropyl, butyl, isobutyl, tert-butyl, etc.) esters of L-arginine and/or D-arginine (e.g., a methyl ester, an ethyl ester, a propyl ester, a butyl ester, etc.) and/or salts thereof, as well as other derivatives of arginine and other nitric oxide donors. For instance, non-limiting examples of pharmaceutically acceptable salts include hydrochloride, glutamate, butyrate, or glycolate (e.g., resulting in L-arginine glutamate, L-arginine butyrate, L-arginine glycolate, D-arginine hydrochloride, D-arginine glutamate, etc.). Still other examples of nitric oxide donors include L-arginine-based compounds such as, but not limited to, L-homoarginine, N-hydroxy-L-arginine, nitrosylated L-arginine, nitrosylated L-arginine, nitrosylated N-hydroxy-L-arginine, nitrosylated N-hydroxy-L-arginine, citrulline, ornithine, linsidomine, nipride, glutamine, etc., and salts thereof (e.g., hydrochloride, glutamate, butyrate, glycolate, etc.), and/or any combination of these and/or other compounds. Still other non-limiting examples of nitric oxide donors include S-nitrosothiols, nitrites, 2-hydroxy-2-nitrosohydrazines, or substrates of various forms of nitric oxide synthase. In some cases, the nitric oxide donor may be a compound that stimulates endogenous production of nitric oxide in vivo. Examples of such compounds include, but are not limited to, L-arginine, substrates of various forms of nitric oxide synthase, certain cytokines, adenosine, bradykinin, calreticulin, bisacodyl, phenolphthalein, OH-arginine, or endothelein, and/or any combination of these and/or other compounds.

Accordingly, it should be understood that, in any of the embodiments described herein that describe L-arginine and/or L-arginine hydrochloride, other nitric oxide donors may also be used instead, or in combination with, L-arginine and/or L-arginine hydrochloride, in other embodiments of the invention.

In some cases, the concentration of the nitric oxide donor within the composition may be tailored to have a duration of effective treatment of at least about 3 hours, at least about 5 hours, or at least about 8 hours or more in certain instances. The duration may also be controlled, for instance, by controlling the concentration of a penetrating agent used in conjunction with the nitric oxide donor. Penetration agents are discussed in detail herein. The actual concentration for a particular application can be determined by those of ordinary skill in the art using no more than routine experimentation, for example, by measuring the amount of transport of the nitric oxide donor as a function of concentration in vitro across cadaver skin or suitable animal models, skin grafts, synthetic model membranes, human models, or the like.

As a particular non-limiting example, in certain embodiments, nitric oxide is provided using L-arginine, for example, at a concentration of at least about 0.5% by weight (wt % or w/v) of L-arginine (optionally with one or more penetrating agents as discussed herein, for example, a penetrating agent able to create a hostile biophysical environment), at least about 0.75 wt %, at least about 1 wt %, at least about 2 wt %, at least about 3 wt %, at least about 5 wt %, at least about 7 wt %, at least about 10 wt %, or at least about 15 wt %. The L-arginine may be present in a suitable delivery vehicle, such as a cream or a lotion. L-arginine may be particularly useful in some cases due to its low toxicity, its high solubility, and/or its low cost. Other examples of nitric oxide donors are discussed in International Patent Application No. PCT/US2005/005726, filed Feb. 23, 2005, entitled "Topical Delivery of a Nitric Oxide Donor to Improve Body and Skin Appearance," by E. T. Fossel, published as WO 2005/081964 on Sep. 9, 2005, incorporated herein by reference.

Without wishing to be bound to any theory, it is generally believed that the flow of the pharmaceutical agent across the skin may slow as it builds up within the tissue. Fick's first law of diffusion suggests that when the concentration inside becomes substantially equal to that outside, passive flow stops. The increased local blood flow may prevent or at least decrease the stoppage of the flow of the pharmaceutical agent. Thus, when the composition is applied to the skin, the pharmaceutical agent exits the vehicle into the tissue more readily, as the pharmaceutical agent is dispersed by flow and does not build up in concentration in the tissue. Thus, in certain embodiments, pharmaceutical agents may be introduced into the skin, for example, ibuprofen and/or an ibuprofen salt.

A hostile biophysical environment of the invention can comprise, in various embodiments, high ionic strength, a high concentration of osmotic agents such as ureas, sugars, or carbohydrates, a high pH environment (e.g., greater than about 9, greater than about 10, greater than about 11, greater than about 12, or greater than about 13), a low pH environment (less than about 5, less than about 4, less than about 3 or less than about 2), highly hydrophobic components, or highly hydrophilic components or other substances that cause an increase in the chemical potential and/or free energy of the pharmaceutical agent, or any combination of two or more of these and/or other compounds. A hydrophobic component may, in some embodiments, have an octanol-water partition coefficient of at least about 100, at least about 1000, at least about $10^4$, at least about $10^5$, or more in some cases. Similarly, a hydrophilic component may have an octanol-water partition coefficient of less than about 0.01, less than about $10^{-3}$, less than about $10^{-4}$, or less than about $10^{-5}$ in some cases.

In some cases, the composition defines the biophysical hostile environment. In other cases, a pharmaceutical agent may be packaged in such a way that it is carried into tissue and/or its charge is neutralized by derivitization and/or by forming a neutral salt. Examples of biophysically hostile environments include, but are not limited to, high ionic strength environments (e.g., by the addition of ureas, sugars, carbohydrates, and/or ionic salts such as lithium chloride, sodium chloride, potassium chloride, calcium chloride, magnesium chloride, choline chloride, sodium fluoride, lithium bromide, etc.), as well as combinations of these and/or other agents, for instance at high ionic strengths (for example, greater than about 0.25 M, greater than about 1 M, greater than about 2 M, greater than about 3 M, greater than about 5 M, greater than about 10 M, greater than about 15 M, greater than about 20 M, greater than about 25 M, etc., or in some cases, between about 0.25 M and about 15 M, between about 5 M and about 15 M, between about 10 M and about 15 M, etc.); high or low pH environments (e.g., by adding pharmaceutically acceptable acids or bases, for example, such that the pH is between about 3 and about 7, between about 3 and about 6, between about 3 and about 5, between about 7 and about 11, between about 8 and about 11, between about 9 and about 11, etc.); or highly hydrophobic environments (e.g., by decreasing water content and increasing lipid, oil and/or wax content of the environment). In some embodiments, the ionic strength is any amount greater than two times the physiological ionic strength of blood.

Other highly charged molecules such as polylysine, polyglutamine, polyaspartate, etc., or copolymers of such highly charged amino acids may also be used in certain embodiments to create the hostile biophysical environment. Non-limiting examples of delivery vehicles which would be carried into tissue includes liposomes or emulsions of collagen, collagen peptides or other components of skin or basement membrane. Non-limiting examples of neutralization of charge include delivery of the pharmaceutical agent in the form or an ester or salt which is electronically neutral. In some embodiments, the hostile biophysical environment may include any two or more of these conditions. For instance, the hostile biophysical environment may include high ionic strength and a high pH or a low pH, a highly hydrophobic environment and a high pH or a low pH, a highly hydrophobic environment that includes liposomes, or the like.

A hostile biophysical environment may also be created in some embodiments by placing a pharmaceutical agent that is relatively highly charged into a hydrophobic, oily environment such as in an oil-based cream or lotion containing little or no water. Absorption may further be aided by combining the use of hostile biophysical environments with the use of penetrating agents, as further described herein.

In one set of embodiments, the composition may be present as an emulsion. As known by those of ordinary skill in the art, an emulsion typically includes a first phase (e.g., a discontinuous phase) contained within a second fluid phase (e.g., a continuous phase). The pharmacological agent (e.g., ibuprofen) may be present in either or both phases. In addition, other materials such as those described herein may be present in the same phase as the pharmacological agent. For instance, when present, the nitric oxide donor, the stabilization polymer, propylene glycol, and/or the polysorbate surfactant may all be present in the same phase as the pharmacological agent, e.g., in the discontinuous phase and/or in the continuous phase.

Another aspect of the present invention is generally directed to compositions for topical delivery having, by weight, at least about 50%, at least about 70%, at least about 80%, at least about 85%, at least about 90%, at least about 95%, or substantially all of the composition comprising water, at least one chloride salt, a nitric oxide donor, a stabilization polymer, propylene glycol, a polysorbate surfactant, and ibuprofen and/or an ibuprofen salt. The composition may also include other components, for instance, glyceryl stearate, cetyl alcohol, squalane, isopropyl myristate, and/or oleic acid, which may form part or all of the balance of the composition. Examples of these and/or other components are described herein.

Water may be present at any suitable concentration, for instance, present at a concentration of at least about 20%, at least about 25%, at least about 30%, at least about 35%, at least about 40%, at least about 45%, or at least about 50% by weight of the composition. In certain embodiments, the water is present at a concentration of about 40.9% by weight of the composition.

Non-limiting examples of chloride salts include sodium, potassium chloride, calcium chloride, magnesium chloride, choline chloride, and the like. In some cases, more than one chloride salt may be present, for example, sodium chloride and potassium chloride. The chloride salt(s) may be present in any suitable concentration, and in some cases, the chloride salt(s) may create a hostile biophysical environment. For instance, the chloride salt(s) may be present at a concentration of at least about 1%, at least about 2%, at least about 3%, at least about 4%, at least about 5%, at least about 6%, at least about 7%, at least about 7.5%, at least about 8%, at least about 9%, at least about 10%, at least about 12%, at least about 15%, at least about 17%, or at least about 20% by weight of the composition.

As a non-limiting example, in one set of embodiments, the composition may consist essentially of water, sodium chloride, a nitric oxide donor, glyceryl stearate, cetyl alcohol, potassium chloride, squalane, a stabilization polymer, isopropyl myristate, oleic acid, propylene glycol, a polysorbate surfactant, and ibuprofen and/or an ibuprofen salt.

As specific non-limiting examples, in some cases, the glyceryl stearate is present at a concentration of about 7% by weight of the composition. In certain cases, the cetyl alcohol is present at a concentration of about 7% by weight of the composition. In one set of embodiments, squalene is present at a concentration of about 4% by weight of the composition. In some instances, potassium chloride is present at a concentration of about 5% by weight of the composition. In one set of embodiments, isopropyl myristate is present at a concentration of about 1% by weight of the composition. In some cases, oleic acid is present at a concentration of about 1% by weight of the composition.

In some embodiments, the present invention is directed to a composition comprising each of the following compounds at concentrations of no more than +20% of the stated concentrations: water at a concentration of about 40.9% weight, sodium chloride at a concentration of about 10% weight, a nitric oxide donor at a concentration of about 7.5% weight, glyceryl stearate at a concentration of about 7% weight, cetyl alcohol at a concentration of about 7% weight, potassium chloride at a concentration of about 5% weight, squalane at a concentration of about 4% weight, a stabilization polymer at a concentration of about 0.8% weight; isopropyl myristate at a concentration of about 1% weight, oleic acid at a concentration of about 1% weight, propylene glycol at a concentration of about 5% weight, a polysorbate surfactant at a concentration of about 2% by weight; and ibuprofen and/or an ibuprofen salt at a concentration of about 7.5% weight.

In some aspects of the invention, a composition of the invention is administered to a subject using a delivery vehicle such as a cream, gel, liquid, lotion, spray, aerosol, or transdermal patch. In one set of embodiments, a composition of the invention may be applied or impregnated in a bandage or a patch applied to the skin of a subject. A "subject," as used herein, means a human or non-human animal. Examples of subjects include, but are not limited to, a mammal such as a dog, a cat, a horse, a donkey, a rabbit, a cow, a pig, a sheep, a goat, a rat (e.g., *Rattus Norvegicus*), a mouse (e.g., *Mus musculus*), a guinea pig, a hamster, a primate (e.g., a monkey, a chimpanzee, a baboon, an ape, a gorilla, etc.), or the like. Such delivery vehicles may be applied to the skin of a subject, such as a human subject. Examples of delivery vehicles are discussed herein. The delivery vehicle may promote transfer into the skin of an effective concentration of the nitric oxide donor and/or the pharmaceutical agent, directly or indirectly. For instance, the delivery vehicle may include one or more penetrating agents, as further described herein. Those of ordinary skill in the art will know of systems and techniques for incorporating a nitric oxide donor and/or a pharmaceutical agent within delivery vehicles such as a cream, gel, liquid, lotion, spray, aerosol, or transdermal patch. In some cases, the concentration of the nitric oxide donor, and/or a pharmaceutical agent in the delivery vehicle can be reduced with the inclusion of a greater amount or concentration of penetrating agent, or increased to lengthen the beneficial effect. In one set of embodiments, the nitric oxide donor and/or the pharmaceutical agent may be used in conjunction with an adjunct, such as theophylline (for example, at 10% weight by volume).

Other materials may be present within the delivery vehicle, for example, buffers, preservatives, surfactants, etc. For instance, the cream may include one or more of water, mineral oil, glyceryl stereate, squalene, propylene glycol stearate, wheat germ oil, glyceryl stearate, isopropyl myristate, steryl stearate, polysorbate 60, propylene glycol, oleic acid, tocopherol acetate, collagen, sorbitan stearate, vitamin A and D, triethanolamine, methylparaben, aloe vera extract, imidazolidinyl urea, propylparaben, PND, and/or BHA.

As specific non-limiting examples, a cream may have one or more of (w/v): water (20-80%), white oil (3-18%), glyceryl stearate (0.25-12%), squalene (0.25-12%), cetyl alcohol (0.1-11%), propylene glycol stearate (0.1-11%), wheat germ oil (0.1-6%), polysorbate 60 (0.1-5%), propylene glycol (0.05-5%), collagen (0.05-5%), sorbitan stearate (0.05-5%), vitamin A (0.02-4%), vitamin D (0.02-4%), vitamin E (0.02-4%), triethanolamine (0.01-4%), methylparaben (0.01-4%), aloe vera extract (0.01-4%), imidazolidinyl urea (0.01-4%), propylparaben (0.01-4%), BHA (0.01-4%), L-arginine hydrochloride (0.25-25%), sodium chloride (0.25-25%), magnesium chloride (0.25-25%), and/or choline chloride (0.25-25%). The percentages of each compound can vary (or the compound may be absent in some cases), for example, 1%, 2%, 3%, 4%, 5%, 6%, 7%, 8%, 9%, 10%, 11%, 12%, 13%, 14%, 15%, 20%, etc.

In another embodiment, the cream may include a pharmaceutical agent, such as ibuprofen, and one or more of the following, in any suitable amount: water (e.g., 20-80%), L-arginine hydrochloride (e.g., 0-25%), sodium chloride (e.g., 0-25%), potassium chloride (e.g., 0-25%), glyeryl steareate (e.g., 0-15%), cetyl alcohol (e.g., 0-15%), squalene (e.g., 0-15%), isopropyl mysterate (e.g., 0-15%), oleic acid (e.g., 0-15%), Tween 20 (e.g., 0-10%), and/or butanediol (e.g., 0-10%). The percentages of each compound can vary (or the compound may be absent in some cases), for example, 1%, 2%, 3%, 4%, 5%, 6%, 7%, 8%, 9%, 10%, 11%, 12%, 13%, 14%, 15%, 20%, etc.

In some embodiments, the cream may include a pharmaceutical agent, and one or more ionic salts at a concentration at least sufficient to produce a hostile biophysical environment with respect to the pharmaceutical agent. For example, the cream may include one or more of (w/v): a charged and/or hydrogen bonding entity (0.001-30%), choline chloride (1-30%), sodium chloride (2-30%), and/or magnesium chloride (1-20% w/v). In another example, the cream may include one or more of (w/v): L-arginine hydrochloride (2.5-25%), choline chloride (10-30%), sodium chloride (5-20%), and/or magnesium chloride (5-20%). In still another example, the cream may include one or more of (w/v): creatine (0.001-30%), inosine (0.001-30%), choline chloride (1-30%), sodium chloride (2-30%), magnesium chloride (1-20%), L-arginine (0.1-25%), and/or theophylline (0.1-20%). In some cases, the cream may also contain L-arginine hydrochloride (0-12.5% w/v) and/or theophylline (0-10% w/v). The percentages of each compound can vary (or the compound may be absent in some cases), for example, 1%, 2%, 3%, 4%, 5%, 6%, 7%, 8%, 9%, 10%, 11%, 12%, 13%, 14%, 15%, 20%, etc. In these examples, choline chloride, sodium chloride, and/or magnesium chloride can be used to provide a high ionic strength environment.

While ibuprofen and/or an ibuprofen salt is described herein, it should be understood that this is by way of example only, and in other embodiments, other pharmaceutical agents may be used instead of, or in addition to, ibuprofen and/or an ibuprofen salt. Non-limiting examples of pharmaceutical agents include small molecules (e.g., having a molecular weight of less than about 2,000 Da, less than about 1,500 Da, or less than about 1,000 Da), peptides (e.g., having less than about 10, less than about 15, less than about 20, or less than about 25 amino acids), proteins (typically larger than peptides), hormones, vitamins, nucleic acids, or the like. Additional examples of suitable pharmaceutical agents for use with the present invention include, but are not limited to, NSAIDs (nonsteroidal anti-inflammatory drugs) such as acetylsalicylic acid, naproxen, celecoxib, refecoxib, etc.; pharmaceutical agents with narcotic action such as morphine, codine, propoxyphene, oxycodone, hydrocodon, or other similar narcotics; pharmaceutical agents for erectile or sexual dysfunction such as yohimbie, alprostadil, sildenafil, cialis, uprima, vardenaifl, or the like; pharmaceutical agents for migraine such as dihydroergotamine and its salts, ergotamine and its salts, surnatripan and its salts, rizatriptan and its salts, zolmitriptan and its salts, etc.; pharmaceutical agents for hair treatment such as finasteride, eflornithine, minoxidil, or the like; or other pharmaceutical agents such as niacin, lidocaine, benzocaine, naproxen, etc. Additional examples include muscle improving agents, for example, creatine or creatine precursors (e.g., creatine phosphate), arginine and/or other nitric oxide donors, and/or ATP precursors such as, inosine, adenosine, inosine, adenine, hypoxanthine, ribose, phosphate (e.g., monosodium phosphate), etc., and/or anabolic steroid agents, such as androstene, DHEA, androstenediol, androstenedione, or the like. Another example is ephedra or its components, such as ephedrine and pseudoephedrine. Yet another example are chemotherapeutic agents or agents for treating cancer and/or viral infections, for example, but not limited to tamoxifen (e.g., for breast cancer treatment), cisplatin, carboplatin and related molecules, cyclophosphamide and related molecules, vinca alkaloids, epipodophyllotoxins including taxol, acyclovir, or the like. For example, the cancer and/or viral infections may be skin cancer, breast cancer, penile cancer, testicular cancer, or other localized cancers, or viral infections, such as herpes.

In certain aspects of the invention, a pharmaceutical agent may be combined with a penetrating agent, i.e., an agent that increases transport of the pharmaceutical agent into the skin, relative to transport in the absence of the penetrating agent. In some embodiments, the penetrating agent may define and/or be combined with a hostile biophysical environment. Examples of penetrating agents include oleoresin capsicum or its constituents, or certain molecules containing heterocyclic rings to which are attached hydrocarbon chains.

Non-limiting examples of penetrating agents include, but are not limited to, cationic, anionic, or nonionic surfactants (e.g., sodium dodecyl sulfate, polyoxamers, etc.); fatty acids and alcohols (e.g., ethanol, oleic acid, lauric acid, liposomes, etc.); anticholinergic agents (e.g., benzilonium bromide, oxyphenonium bromide); alkanones (e.g., n-heptane); amides (e.g., urea, N,N-dimethyl-m-toluamide); fatty acid esters (e.g., n-butyrate); organic acids (e.g., citric acid); polyols (e.g., ethylene glycol, glycerol); sulfoxides (e.g., dimethylsulfoxide); terpenes (e.g., cyclohexene); ureas; sugars; carbohydrates or other agents. In certain embodiments, the penetrating agent includes a salt, e.g., as described herein.

Thus, another aspect of the invention provides for the delivery of pharmaceutical agents (e.g., drugs, biological compounds, etc.) into the body, and such treatments may be systemic or localized, e.g., directed to a specific location of the body, such as the head, one or more specific muscles, the genitals, etc., depending on the specific application.

In one set of embodiments, pharmaceutical agents are introduced to aid in treatment of medical conditions or diseases, and the symptoms associated thereof. In some embodiments, the invention provides for the treatment of medical conditions or diseases and/or ailments using pharmaceutical agents (for example, to treat a subject diagnosed with a medical condition or disease), and in some cases, the invention provides for the delivery of a minimum amount of pharmaceutical agents to provide effective levels of medication to an effected area topically while limiting side effects. In some cases, the effective dosage of the pharmaceutical agent may be lower than the effective dosage of the pharmaceutical agent when taken orally. Other embodiments of the invention provide methods for treating pain, for example, pain from migraine, pain from arthritis, other headaches, joint pain, muscle pain and other types of pain. Accordingly, in some embodiments, a composition may be topically applied to a specific location of the body, e.g., to a site of pain. Also, in certain cases, a composition as described herein may be used in the preparation of a medicament for treatment of pain, or other diseases or conditions as discussed herein.

In another aspect, the present invention is directed to a kit including one or more of the compositions discussed herein. A "kit," as used herein, typically defines a package or an assembly including one or more of the compositions of the invention, and/or other compositions associated with the invention, for example, as described herein. Each of the compositions of the kit may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, and the like, for example, for using, administering, modifying, assembling, storing, packaging, preparing, mixing, diluting, and/or preserving the compositions components for a particular use, for example, to a sample and/or a subject.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. In some cases, the instructions may also include instructions for the delivery and/or administration of the compositions, for example, for a particular use, e.g., to a sample and/or a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

In some embodiments, the present invention is directed to methods of promoting one or more embodiments of the invention as discussed herein, for example, methods of promoting the making or use of compositions such as those discussed above, methods of promoting kits as discussed above, or the like. As used herein, "promoted" includes all methods of doing business including, but not limited to, methods of selling, advertising, assigning, licensing, contracting, instructing, educating, researching, importing, exporting, negotiating, financing, loaning, trading, vending, reselling, distributing, repairing, replacing, insuring, suing, patenting, or the like that are associated with the systems, devices, apparatuses, articles, methods, compositions, kits, etc. of the invention as discussed herein. Methods of promotion can be performed by any party including, but not limited to, personal parties, businesses (public or private), partnerships, corporations, trusts, contractual or sub-contractual agencies, educational institutions such as colleges and universities, research institutions, hospitals or other clinical institutions, governmental agencies, etc. Promotional activities may include communications of any form (e.g., written, oral, and/or electronic communications, such as, but not limited to, e-mail, telephonic, Internet, Web-based, etc.) that are clearly associated with the invention.

In one set of embodiments, the method of promotion may involve one or more instructions. As used herein, "instructions" can define a component of instructional utility (e.g., directions, guides, warnings, labels, notes, FAQs or "frequently asked questions," etc.), and typically involve written instructions on or associated with the invention and/or with the packaging of the invention. Instructions can also include instructional communications in any form (e.g., oral, electronic, audible, digital, optical, visual, etc.), provided in any manner such that a user will clearly recognize that the instructions are to be associated with the invention, e.g., as discussed herein.

The following documents are incorporated herein by reference: International Patent Application No. PCT/US98/19429, filed Sep. 17, 1998, entitled "A Delivery of Arginine to Cause Beneficial Effects," by E. Fossel, published as WO 99/13717 on Mar. 25, 1999; International Patent Application No. PCT/US2005/005726, filed Feb. 23, 2005, entitled "Topical Delivery of a Nitric Oxide Donor to Improve Body and Skin Appearance," by E. Fossel, et al., published as WO 2005/081964 on Sep. 9, 2005; International Patent Application No. PCT/US2005/013228, filed Apr. 19, 2005, entitled "Transdermal Delivery of Beneficial Substances Effected by a Hostile Biophysical Environment," by E. Fossel, published as WO 2005/102282 on Nov. 3, 2005; and International Patent Application No. PCT/US2005/013230, filed Apr. 19, 2005, entitled "Beneficial Effects of Increasing Local Blood Flow," by E. Fossel, published as WO 2005/102307 on Nov. 3, 2005.

Also incorporated by reference herein are U.S. patent application Ser. No. 08/932,227, filed Sep. 17, 1997, entitled "Topical Delivery of Arginine of Cause Beneficial Effects," by E. T. Fossel, published as 2002/0041903 on Apr. 11, 2002; U.S. patent application Ser. No. 10/201,635, filed Jul. 22, 2002, entitled "Topical Delivery of L-Arginine to Cause Beneficial Effects," by E. T. Fossel, published as 2003/0028169 on Feb. 6, 2003; U.S. patent application Ser. No. 10/213,286, filed Aug. 5, 2002, entitled "Topical and Oral Arginine to Cause Beneficial Effects," by E. T. Fossel, published as 2003/0018076 on Jan. 23, 2003; U.S. Pat. No. 5,895,658, issued Apr. 20, 1999, entitled "Topical Delivery of L-Arginine to Cause Tissue Warming," by E. T. Fossel; U.S. Pat. No. 5,922,332, issued Jul. 13, 1999, entitled "Topical Delivery of Arginine to Overcome Pain," by E. T. Fossel; U.S. Pat. No. 6,207,713, issued Mar. 27, 2001, entitled "Topical and Oral Delivery of Arginine to Cause Beneficial Effects," by E. T. Fossel; and U.S. Pat. No. 6,458,841, issued Oct. 1, 2002, entitled "Topical and Oral Delivery of Arginine to Cause Beneficial Effects," by E. T. Fossel.

The following examples are intended to illustrate certain embodiments of the present invention, but do not exemplify the full scope of the invention.

Example 1

This example illustrates one method of preparing a transdermal formula of the invention including ibuprofen. The final composition is shown in Table 1. Of course, those of ordinary skill in the art will understand that percentages other than the ones listed below are also possible, according to other embodiments of the invention.

TABLE 1

| Ingredient | % w/w |
|---|---|
| Water | 40.9 |
| Sodium Chloride | 10.0 |
| L-Arginine Hydrochloride | 7.5 |
| Ibuprofen (sodium salt) | 7.5 |
| Glyceryl Stearate (SE) | 7.0 |
| Cetyl Alcohol | 7.0 |
| Potassium Chloride | 5.0 |
| Squalane | 4.0 |
| Xanthan Gum | 0.8 |
| Isopropyl Myristate | 1.0 |
| Oleic Acid | 1.0 |
| Propylene Glycol | 5.0 |
| Polysorbate-20 | 2.0 |

To prepare the formulation in this example, sodium chloride, potassium chloride, L-arginine and ibuprofen were mixed in water, then heated to 74° C. with rapid mixing. In a separate container, the remaining ingredients were mixed together and heated to 74° C. The other ingredients were then added to the water phase at 74° C. with rapid mixing. The mixture was then cooled to room temperature with continued mixing. At this point, an emulsion formed with a relatively thin consistency. The emulsion was then homogenized at high speed at room temperature to thicken the consistency.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A transdermal patch for application to the skin of a subject, the transdermal patch comprising a composition comprising:
   an ionic strength of at least about 0.25 M;
   a stabilization polymer comprising xanthan gum;
   propylene glycol;
   a polysorbate surfactant comprising polysorbate 20; and
   ibuprofen and/or an ibuprofen salt.

2. The transdermal patch of claim 1, wherein the composition further comprises a nitric oxide donor.

3. The transdermal patch of claim 2, wherein the nitric oxide donor comprises L-arginine and/or an L-arginine salt.

4. The transdermal patch of claim 3, wherein the nitric oxide donor comprises L-arginine.

5. The transdermal patch of claim 3, wherein the nitric oxide donor comprises L-arginine hydrochloride.

6. The transdermal patch of claim 2, wherein the nitric oxide donor is present at at least about 0.5% by weight of the composition.

7. The transdermal patch of claim 1, wherein the composition comprises sodium chloride.

8. The transdermal patch of claim 7, wherein the sodium chloride is present at at least about 5% by weight of the composition.

9. The transdermal patch of claim 1, wherein the composition comprises one or more salts selected from the group consisting of choline chloride, magnesium chloride, lithium chloride, and calcium chloride.

10. The transdermal patch of claim 1, wherein the composition is stable when exposed to a temperature of 40° C. for at least about 4 weeks.

11. The transdermal patch of claim 1, wherein the composition further comprises a penetration agent.

12. The transdermal patch of claim 1, wherein the composition comprises citric acid.

13. The transdermal patch of claim 1, wherein the composition has an ionic strength of at least about 1 M.

14. The transdermal patch of claim 1, wherein the composition has a pH of between about 5 and about 9.

15. The transdermal patch of claim 1, wherein the composition is capable of driving the ibuprofen and/or ibuprofen salt through stratum corneum.

16. The transdermal patch of claim 1, wherein the composition further comprises a package containing the nitric oxide donor, the package being selected from the group consisting of liposomes, emulsions of collagen, collagen peptides, and combinations thereof.

17. The transdermal patch of claim 1, wherein the stabilization polymer is present at at least about 0.5% by weight of the composition.

18. The transdermal patch of claim 1, wherein the propylene glycol is present at at least about 1% by weight of the composition.

19. The transdermal patch of claim 1, wherein the polysorbate surfactant is present at at least about 1% by weight of the composition.

20. The transdermal patch of claim 1, wherein the ibuprofen and/or ibuprofen salt is present at at least about 0.1% by weight of the composition.

21. The transdermal patch of claim 1, wherein the composition further comprises one or more of glyceryl stearate, cetyl alcohol, squalene, isopropyl myristate, and oleic acid.

22. A method of topically treating or reducing inflammation or pain in a subject, comprising applying the transdermal patch of claim 1 to a site of inflammation or pain of the subject.

23. The method of claim 22, wherein the subject is human.

* * * * *